United States Patent
Hourmand et al.

(10) Patent No.: US 9,474,866 B2
(45) Date of Patent: *Oct. 25, 2016

(54) AUTO-INJECTOR

(75) Inventors: Yannick Hourmand, Haslingfield (GB); Simon Francis Brereton, Cambridgeshire (GB); Thomas Mark Kemp, Ashwell (GB); Rosie Burnell, Cambridge (GB); Matthew Ekman, Cheshire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 695 days.

This patent is subject to a terminal disclaimer.

(21) Appl. No.: 13/996,145

(22) PCT Filed: Dec. 21, 2011

(86) PCT No.: PCT/EP2011/073507
§ 371 (c)(1),
(2), (4) Date: Jun. 20, 2013

(87) PCT Pub. No.: WO2012/085026
PCT Pub. Date: Jun. 28, 2012

(65) Prior Publication Data
US 2013/0296796 A1 Nov. 7, 2013

Related U.S. Application Data

(60) Provisional application No. 61/432,722, filed on Jan. 14, 2011.

(30) Foreign Application Priority Data

Dec. 21, 2010 (EP) .................................... 10196072

(51) Int. Cl.
*A61M 5/32* (2006.01)
*A61M 5/20* (2006.01)
(Continued)

(52) U.S. Cl.
CPC ........... *A61M 5/326* (2013.01); *A61M 5/2033* (2013.01); *A61M 5/24* (2013.01); *A61M 5/46* (2013.01);
(Continued)

(58) Field of Classification Search
CPC ............. A61M 5/326; A61M 5/3269; A61M 5/3271; A61M 5/3272; A61M 5/2033; A61M 2005/3261; A61M 2005/3267; A61M 2005/3263; A61M 2005/3264; A61M 2005/206; A61M 2005/208
See application file for complete search history.

(56) References Cited

U.S. PATENT DOCUMENTS 5,681,291 A * 10/1997 Galli .................... A61M 5/2033
604/156
(Continued)

FOREIGN PATENT DOCUMENTS

WO 2005070481 A1 4/2005
WO 2005097238 A2 10/2005

*Primary Examiner* — Andrew Gilbert
(74) *Attorney, Agent, or Firm* — Fish & Richardson P.C.

(57) ABSTRACT

The invention refers to an auto-injector for delivering a liquid medicament, comprising:
an elongate housing arranged to contain a syringe with a hollow injection needle and a stopper, wherein the syringe is slidably arranged with respect to the housing, spring means capable of, upon activation:
pushing the needle from a covered position inside the housing into an advanced position for insertion into the injection site,
operating the syringe to inject the dose of medicament, and
advancing a needle shroud over the needle for providing needle safety,
activating means arranged to lock and release the spring means,
wherein the spring means is a single drive spring in the shape of a compression spring grounded distally in the housing and proximally bearing against a thrust collar arranged to transmit load from the spring means via a plunger to the syringe and/or the stopper for needle insertion and injection, wherein the plunger is engageable to the thrust collar for joint axial translation, wherein the plunger is disengageable from the thrust collar on relative rotation so as to allow the thrust collar to be advanced further by the drive spring in order to engage the needle shroud for advancing it over the needle.

14 Claims, 6 Drawing Sheets

(51) Int. Cl.
    *A61M 5/24* (2006.01)
    *A61M 5/46* (2006.01)
(52) U.S. Cl.
    CPC .. *A61M 2005/206* (2013.01); *A61M 2005/208* (2013.01); *A61M 2205/581* (2013.01); *A61M 2205/582* (2013.01)

(56) References Cited

U.S. PATENT DOCUMENTS

| | | | | |
|---|---|---|---|---|
| 6,099,503 | A * | 8/2000 | Stradella | A61M 5/2033 604/131 |
| 6,620,137 | B2 * | 9/2003 | Kirchhofer | A61M 5/2033 604/187 |
| 6,884,237 | B2 * | 4/2005 | Asbaghi | A61M 5/3272 604/192 |
| 9,272,098 | B2 * | 3/2016 | Hourmand | A61M 5/3257 |
| 2002/0095120 | A1 * | 7/2002 | Larsen | A61M 5/2033 604/187 |
| 2003/0040725 | A1 * | 2/2003 | Hommann | A61M 5/326 604/263 |
| 2007/0112310 | A1 * | 5/2007 | Lavi | A61M 5/2033 604/245 |
| 2008/0147006 | A1 * | 6/2008 | Brunnberg | A61M 5/2033 604/136 |
| 2008/0262438 | A1 * | 10/2008 | Bollenbach | A61M 5/2033 604/207 |
| 2009/0149809 | A1 * | 6/2009 | Bollenbach | A61M 5/2033 604/111 |
| 2009/0234297 | A1 * | 9/2009 | Jennings | A61M 5/2033 604/195 |
| 2010/0268170 | A1 * | 10/2010 | Carrel | A61M 5/2033 604/198 |
| 2010/0280460 | A1 * | 11/2010 | Markussen | A61M 5/2033 604/195 |

* cited by examiner

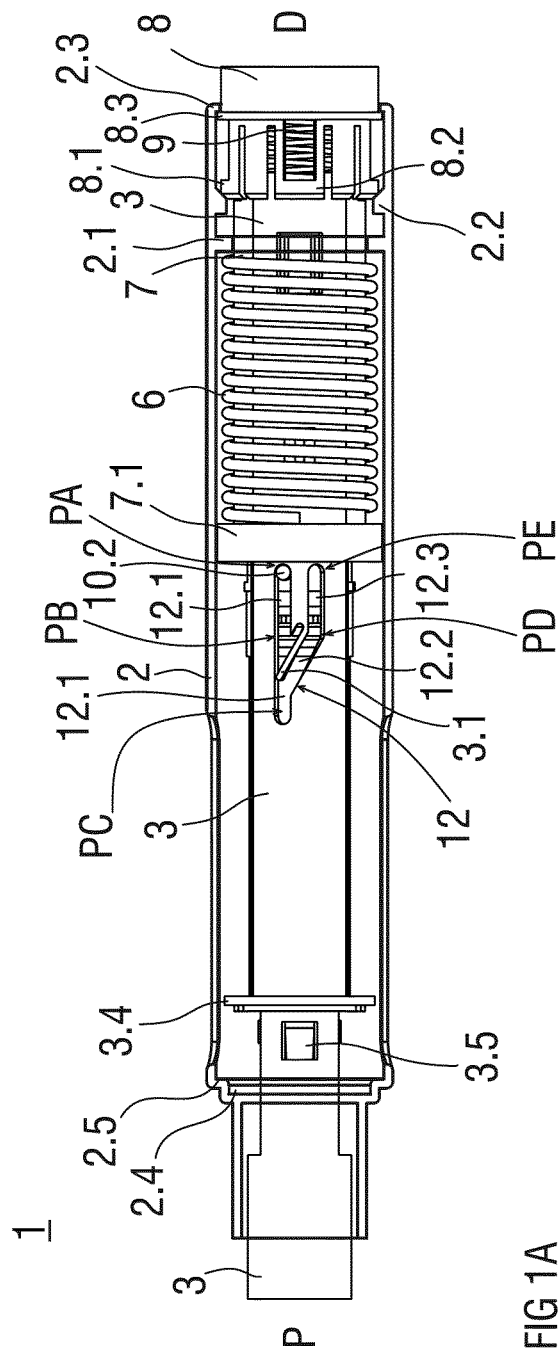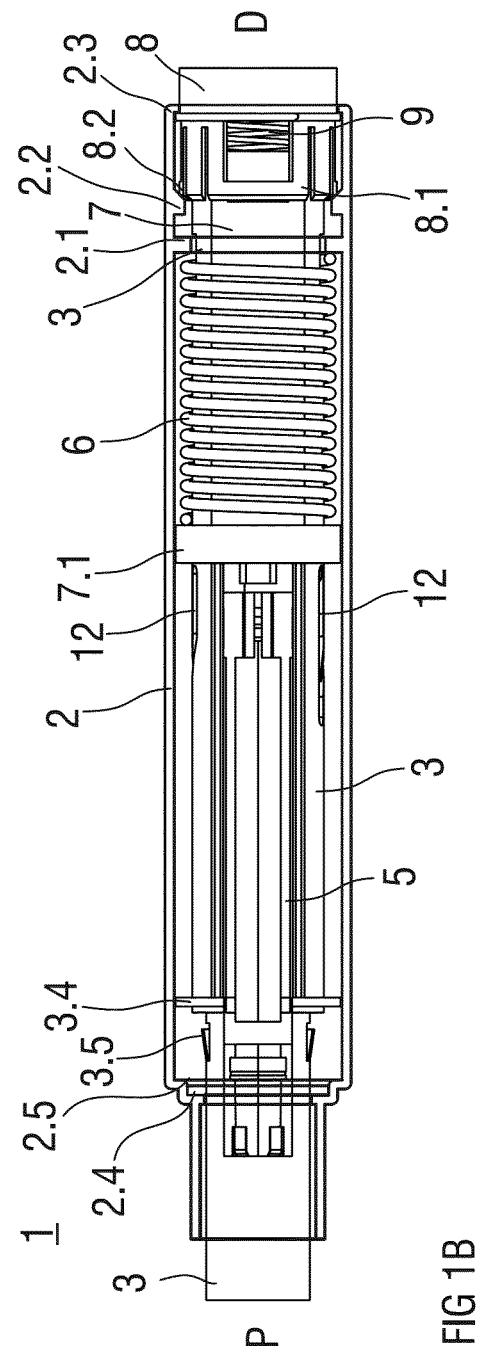
FIG 1A
FIG 1B

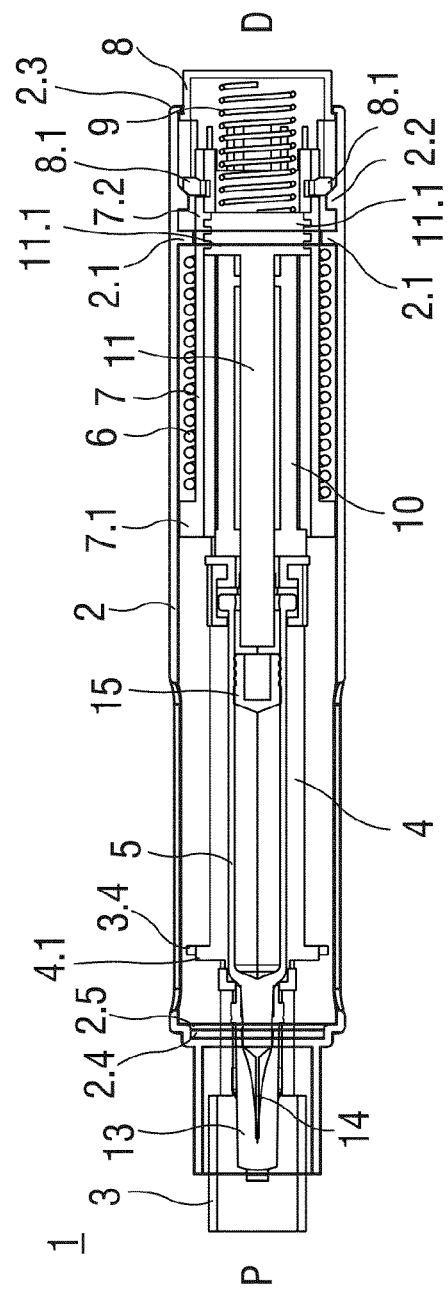
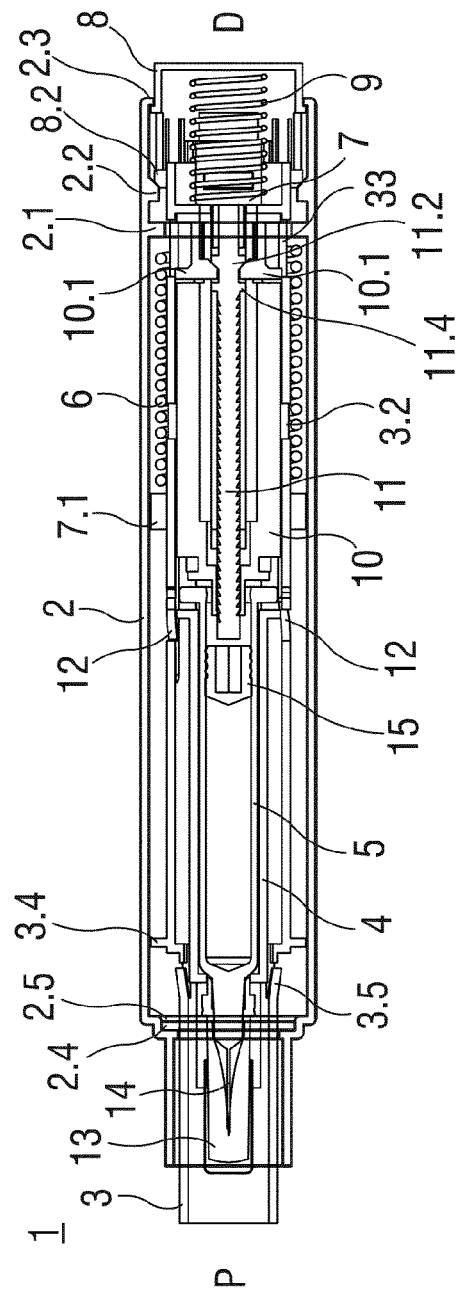
FIG 2A
FIG 2B

AUTO-INJECTOR

CROSS REFERENCE TO RELATED APPLICATIONS

The present application is a U.S. National Phase Application pursuant to 35 U.S.C. §371 of International Application No. PCT/EP2011/073507 filed Dec. 21, 2011, which claims priority to European Patent Application No. 10196072.2 filed Dec. 21, 2010 and U.S. Provisional Patent Application No. 61/432,722 filed Jan. 14, 2011. The entire disclosure contents of these applications are herewith incorporated by reference into the present application.

FIELD OF INVENTION

The invention relates to an auto-injector for administering a dose of a liquid medicament according to the preamble of claim 1.

BACKGROUND

Administering an injection is a process which presents a number of risks and challenges for users and healthcare professionals, both mental and physical.

Injection devices (i.e. devices capable of delivering medicaments from a medication container) typically fall into two categories—manual devices and auto-injectors.

In a manual device—the user must provide the mechanical energy to drive the fluid through the needle. This is typically done by some form of button/plunger that has to be continuously pressed by the user during the injection. There are numerous disadvantages to the user from this approach. If the user stops pressing the button/plunger then the injection will also stop. This means that the user can deliver an under dose if the device is not used properly (i.e. the plunger is not fully pressed to its end position). Injection forces may be too high for the user, in particular if the patient is elderly or has dexterity problems.

The extension of the button/plunger may be too great. Thus it can be inconvenient for the user to reach a fully extended button. The combination of injection force and button extension can cause trembling/shaking of the hand which in turn increases discomfort as the inserted needle moves.

Auto-injector devices aim to make self-administration of injected therapies easier for patients. Current therapies delivered by means of self-administered injections include drugs for diabetes (both insulin and newer GLP-1 class drugs), migraine, hormone therapies, anticoagulants etc.

Auto-injectors are devices which completely or partially replace activities involved in parenteral drug delivery from standard syringes. These activities may include removal of a protective syringe cap, insertion of a needle into a patient's skin, injection of the medicament, removal of the needle, shielding of the needle and preventing reuse of the device. This overcomes many of the disadvantages of manual devices. Injection forces/button extension, hand-shaking and the likelihood of delivering an incomplete dose are reduced. Triggering may be performed by numerous means, for example a trigger button or the action of the needle reaching its injection depth. In some devices the energy to deliver the fluid is provided by a spring.

US 2002/0095120 A1 discloses an automatic injection device which automatically injects a pre-measured quantity of fluid medicine when a tension spring is released. The tension spring moves an ampoule and the injection needle from a storage position to a deployed position when it is released. The content of the ampoule is thereafter expelled by the tension spring forcing a piston forward inside the ampoule. After the fluid medicine has been injected, torsion stored in the tension spring is released and the injection needle is automatically retracted back to its original storage position.

SUMMARY

It is an object of the present invention to provide an improved auto-injector.

The object is achieved by an auto-injector according to claim 1.

Preferred embodiments of the invention are given in the dependent claims.

In the context of this specification the term proximal refers to the direction pointing towards the patient during an injection while the term distal refers to the opposite direction pointing away from the patient. The terms clockwise and counter-clockwise refer to rotations seen from a distal end of the auto-injector.

An auto-injector for delivering a liquid medicament according to the invention comprises an elongate housing arranged to contain a syringe with a hollow injection needle and a stopper for sealing the syringe and displacing the medicament. The housing has a distal end and a proximal end with an orifice intended to be applied against an injection site, e.g. a patient's skin. The syringe is slidably arranged with respect to the housing. Furthermore the auto-injector comprises:

spring means capable of, upon activation:
pushing the needle from a covered position inside the housing into an advanced position through the orifice and past the proximal end for insertion into the injection site,
operating the syringe to inject the dose of medicament, and
advancing a needle shroud over the needle for providing post injection needle safety,
activating means arranged to lock the spring means in a pressurized state prior to manual operation and capable of, upon manual operation, releasing the spring means for needle insertion and injection.

The spring means is a single drive spring in the shape of a compression spring grounded distally in the housing and proximally bearing against a thrust collar arranged to transmit load from the spring means via a plunger to the syringe and/or the stopper for needle insertion and injection. The plunger is engageable to the thrust collar for joint axial translation in a longitudinal direction. The plunger is disengageable from the thrust collar on relative rotation so as to allow the thrust collar to be advanced further by the drive spring in order to engage the needle shroud for advancing it over the needle.

The single compression spring is used for inserting the needle, fully emptying the syringe and advancing the needle shroud. Thus a second spring is not required. When the injection is at least nearly finished or when the user removes the auto-injector from the injection site mid injection, the plunger is rotated out of engagement with the thrust collar allowing the thrust collar to translate without the plunger for advancing the needle shroud. Decoupling the plunger also serves for stopping the injection immediately thus avoiding medicament leaking out of the needle tip after removal from the injection site.

The auto-injector according to the invention has a particularly low part count compared to most conventional auto-injectors. The use of just one compression spring reduces the amount of metal needed and thus consequently reduces weight and manufacturing costs.

The needle shroud may be biased in a proximal direction so as to be in an initial position protruding from the proximal end in an initial state prior to injection. The activating means may comprise a trigger button interlocked to the needle shroud in such a manner that the needle shroud prevents manual operation of the trigger button when in the initial position, wherein the needle shroud is arranged to release the interlock on translation in a distal direction into a depressed position so as to allow manual operation of the trigger button.

This results in an auto-injector with a sequenced operation. In the as delivered state the interlock sleeve is in its initial position protruding from the proximal end of the housing. The syringe and needle are in their retracted position. In order to trigger an injection the auto-injector has to be pressed with its proximal end against an injection site, e.g. a patient's skin in a manner to translate the interlock sleeve in the distal direction into the housing. This translation allows the trigger button to be actuated for eventually releasing the drive spring and starting an injection cycle. The probability for inadvertent operation of the auto-injector decreases due to the requirement of two sequenced user actions, pressing the auto-injector against the injection site and operating the activating means.

The needle shroud may be arranged to rotate the plunger on removal of the auto-injector from the injection site by translation from the depressed position into the initial position due to the bias, wherein the thrust collar is arranged to translate the needle shroud further into a needle safe position. The bias, which may be a small spring or an integrally moulded resilient part on the needle shroud does not advance the needle shroud into the needle safe position. It just serves for allowing the needle shroud to be used as a skin contact sensor indicating if the auto-injector is being pressed against the skin for allowing depression of the trigger button to start the injection cycle and also indicating if the auto-injector has been removed from the skin during injection or at the end of injection for triggering the needle shroud advance.

The plunger may be slidably arranged within and keyed to a coupling carrier for joint rotation, wherein the coupling carrier is coupled to the syringe for joint translation. The coupling carrier is connected to the needle shroud by a pin engaged in a shifting gate with a one-way feature in such manner that the pin is guided in a longitudinal main track of the shifting gate on translation of the needle shroud from the initial position into the depressed position and on translation of the syringe during needle insertion, thus preventing relative rotation of the plunger and the needle shroud. The one-way feature is arranged to be passed by the pin on needle insertion so the pin cannot return the same way. Instead, the one-way feature is arranged to guide the pin into a bevel track at a bifurcation of the shifting gate on removal from the injection site and translation of the needle shroud from the depressed position into the initial position thus rotating the coupling carrier and the plunger for disengaging it from the thrust collar.

The plunger may comprise a teethed transversal arm at the distal end engageable in corresponding teeth on an inner surface of the thrust collar in the initial state until removal from skin and consequent relative rotation of the plunger and the thrust collar. The coupling carrier exhibits a longitudinal slot extending from its distal end almost to its proximal end, the slot having a width corresponding to a width of the transversal arm so as to key the plunger to the coupling carrier for joint rotation while allowing relative translation. The engagement of the teeth may be replaced by any other engagement coupling the plunger to the thrust collar for joint translation and decoupling them on relative rotation.

At least one resilient arm on the coupling carrier may be arranged to engage a plunger shoulder in the plunger in a manner to couple the plunger and the coupling carrier for joint axial translation. The resilient arm and the plunger shoulder are in a ramped engagement so as to deflect the resilient arm outwards on axial load for decoupling the plunger from the coupling carrier. The needle shroud, extending over the coupling carrier is arranged to outwardly support the resilient arm so as to prevent outward deflection and decoupling during needle insertion. Thus, when the trigger button is depressed the spring force forwarded by the plunger does not yet press against the stopper but against the coupling carrier and syringe for forwarding them. Consequently, a so called wet injection is avoided, i.e. the liquid medicament is not leaking out of the hollow needle before the needle is almost fully inserted. At least one first aperture is provided in the thrust collar for allowing outward deflection of the resilient arms when the needle has at least almost reached an injection depth near the end of needle insertion, since the coupling carrier translates relative to the needle shroud during needle insertion. This allows the plunger shoulder to slip behind the resilient arm and to switch load of the drive spring from the syringe to the stopper. The longitudinal position of the aperture defines the moment to start injecting the medicament.

The trigger button may be arranged at the distal end of the housing in a manner to trigger an injection on depression into the housing in the proximal direction against the bias of a control spring arranged between the trigger button and the needle shroud for biasing the trigger button and the needle shroud against each other into their respective initial positions. The trigger button may likewise be arranged at a different position.

The thrust collar may exhibit at least one window for engaging a respective resilient first latch on the trigger button, wherein the first latch is in a ramped engagement with the thrust collar so as to deflect it outwards on axial load for disengaging it from the thrust collar. A second rib is arranged in the housing for preventing outward deflection of the first latch until the trigger button is depressed. The first latch is arranged to be dislocated from the second rib on depression of the trigger button so as to allow outward deflection when the trigger button is at least almost fully depressed for releasing the drive spring.

At least one resilient second latch may be arranged on the trigger button for proximally abutting against the second rib. The second latch and the second rib are in a ramped engagement so as to deflect the second latch inwards on axial load. The needle shroud is arranged to inwardly support the second latch in the initial position so as to prevent inward deflection. The needle shroud exhibits at least one second aperture arranged to be moved inwardly behind the second latch for allowing inward deflection in the depressed position of the needle shroud. This ensures a sequenced operation of the auto-injector, requiring the user to first depress the needle shroud and then the trigger button.

The plunger may comprise a rack feature for generating an audible and/or tactile feedback when translating relative to the coupling carrier having a corresponding feature for engaging the rack feature. When properly instructed the user can thus tell if the injection is taking place so they have to keep the auto-injector pressed against the injection site as long as there is a noise or vibration or if the entire contents of the syringe have been delivered as the noise or vibration stops so the auto-injector can safely be removed from the injection site. This improves compliance with the medication.

A syringe carrier may be arranged to hold the syringe and support it at its proximal end, wherein the syringe carrier is translatable in the longitudinal direction within the housing. The syringe carrier is coupled to the coupling carrier for joint axial translation in the longitudinal direction. Supporting the syringe at the proximal end is preferred over support at the finger flanges since the finger flanges are more frangible under load while the proximal or front end of the syringe is more robust. While translation of the syringe in the syringe carrier in the proximal direction is prevented by that support translation in the distal direction may be prevented by friction between the syringe and syringe carrier tight-fitting with each other.

The needle shroud may comprise at least one outwardly biased resilient clip arranged to engage to the housing in the needle safe position for preventing translation of the needle shroud in the distal direction. This reduces the risk of post injection needle stick injuries.

The trigger button may be arranged to be locked in the housing after having been depressed. This indicates that the auto-injector has been used thus avoiding attempts to re-use it and preventing cross contamination with used auto-injectors.

The first latch may be in a ramped engagement with the thrust collar wedging the first latch in position between the second rib and the thrust collar. The wedged engagement of the first latch between the second rib and the thrust collar is arranged to allow depression of the trigger button, wherein on at least partial depression of the trigger button the first latch is forced past the ramp on the second rib releasing the wedged engagement and allowing the drive spring to pull the trigger button fully into the depressed position. This prevents the user from hesitantly depressing the trigger button halfway leaving the auto-injector in an undefined state neither triggered nor safe.

The auto-injector may preferably be used for subcutaneous or intra-muscular injection, particularly for delivering one of an analgetic, an anticoagulant, insulin, an insulin derivate, heparin, Lovenox, a vaccine, a growth hormone, a peptide hormone, a protein, antibodies and complex carbohydrates.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein:

FIG. 1 are lateral views of an auto-injector prior to an injection in an initial state, FIG. 2 are longitudinal sections of the auto-injector in the initial state, FIG. 3 are longitudinal sections of the auto-injector with a needle shroud depressed.

Corresponding parts are marked with the same reference symbols in all figures.

DETAILED DESCRIPTION

Figure 3A:
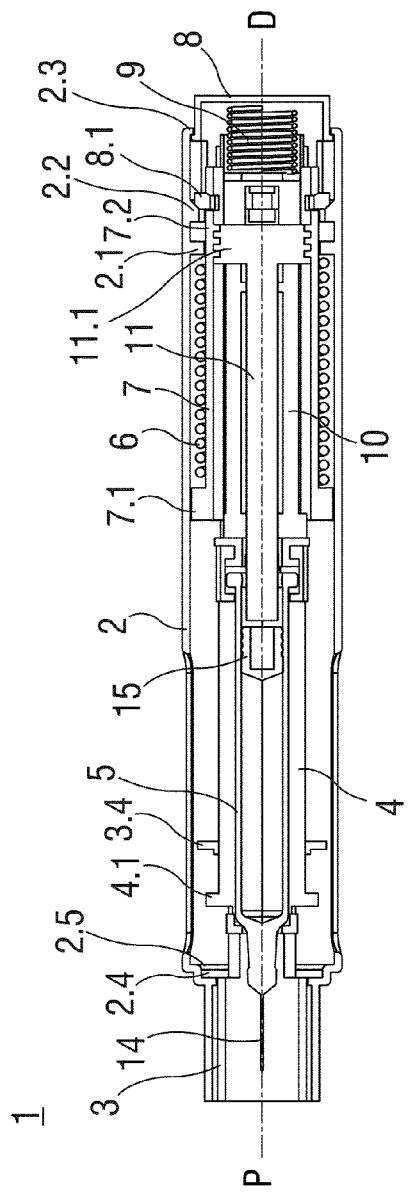

FIGS. 1A and 1B show two lateral views an auto-injector 1 for delivering a liquid medicament prior to use in an initial state, the auto-injector 1 having an elongate, essentially cylindrical housing 2, which is shown transparent for clarity. FIGS. 2A and 2B are corresponding longitudinal sections. The sectional planes shown are oriented perpendicularly with respect to each other. The auto-injector 1 comprises the housing 2, a needle shroud 3 extending through almost the entire housing 2 and a syringe carrier 4 arranged to hold a syringe 5 and support it at its proximal end. The syringe carrier 4 is translatable in a longitudinal direction within the housing 2. A drive spring 6 in the shape of a compression spring is arranged in the housing 2, distally grounded in the housing 2 by bearing against a first rib 2.1. A proximal end of the drive spring 6 bears against a shoulder 7.1 on a thrust collar 7. The thrust collar 7 is keyed with the needle shroud 3 in a manner to prevent them from rotating independently but allowing relative translation. The shoulder 7.1 is arranged around the needle shroud 3. A trigger button 8 is arranged at a distal end D of the auto-injector 1 in a manner to trigger an injection on depression into the housing 2 in a proximal direction P against the bias of a control spring 9. The control spring 9 bears against the trigger button 8 and against the needle shroud 3. In the initial state the trigger button 8 is in a distal position defined by an outward trigger shoulder 8.3 abutted against an inward distal housing shoulder 2.3. Hence, the control spring 9 pushes the needle shroud 3 in the proximal direction P.

Figure 4:
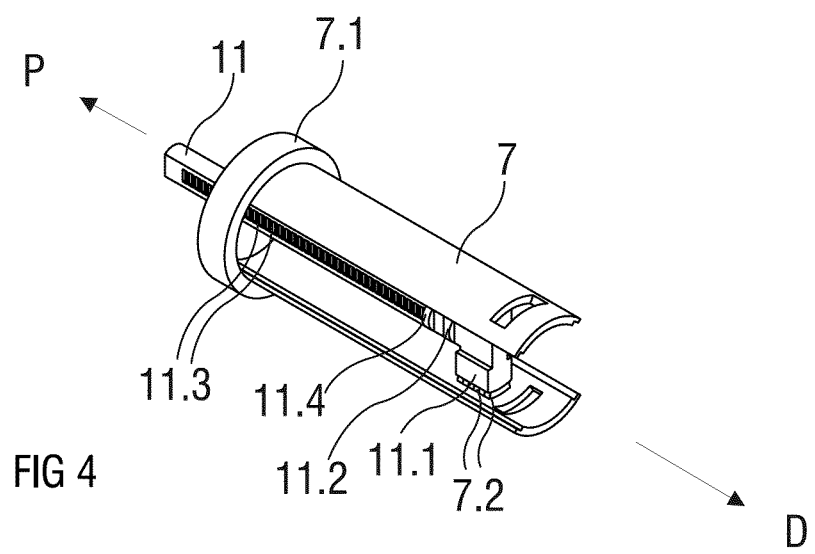
FIG. 4 is an isometric detail view with a collar and a plunger.

A coupling carrier 10 is arranged inside the needle shroud 3 proximally from the syringe carrier 4 and coupled to it for joint axial translation. A plunger 11 for pushing on a stopper 15 in the syringe 5 is arranged inside the coupling carrier 10. The plunger 11 comprises a toothed transversal arm 11.1 at the distal end engaged in corresponding teeth 7.2 on the inner surface of the thrust collar 7 (cf. FIG. 4). The transversal arm 11.1 may be disengaged from the teeth 7.2 by rotating the plunger 11 relative to the thrust collar 7. The coupling carrier 10 exhibits a longitudinal slot extending from its distal end almost to its proximal end, the slot having a width corresponding to the width of the transversal arm 11.1 so as to key the plunger 11 to the coupling carrier 10 for joint rotation while allowing relative translation in the longitudinal direction. Two resilient arms 10.1 on the coupling carrier 10 are arranged to engage a first plunger shoulder 11.2 in the plunger 11 in a manner to couple the plunger 11 and the coupling carrier 10 for joint axial translation. The resilient arms 10.1 and the first plunger shoulder 11.2 are in a ramped engagement so as to deflect the resilient arms 10.1 outwards on axial load for decoupling the plunger 11 from the coupling carrier 10. The needle shroud 3 is arranged to outwardly support the resilient arms 10.1 so as to prevent outward deflection and decoupling in some positions, wherein first apertures 3.2 are provided in the thrust collar 7 for allowing outward deflection of the resilient arms 10.1 at a defined position. A second plunger folder 11.4 proximally from the first plunger shoulder 11.2 for holding the plunger 11 in the correct position during assembly of the auto-injector 1.

A shifting gate 12 for guiding a pin 10.2 on the coupling carrier 10 is arranged in the shape of an aperture in the needle shroud 3. The shifting gate 12 comprises a longitudinal main track 12.1 whose distal end defines a position PA for the pin 10.2 whereas the proximal end of the longitudinal main track 12.1 defines a position PC. A position PB of the pin 10.2 is defined about halfway between the positions PA and PC. Between positions PA and PB the shifting gate 12 bifurcates into a bevel track 12.2 ending in a short longitudinal track 12.3 parallel to the main track 12.1 and a bout half its length. The distal end of the short longitudinal track 12.3 defines a position PE, wherein the relative positions of the coupling carrier 10 and the needle shroud 3 are equal with respect to translation with the pin in positions PA and PE, however they are slightly rotated relative to each other. A position PD is defined where the bevel track 12.2 meets the short longitudinal track 12.3 at about the same translative position as position PB but slightly rotated. A resilient latch 3.1 originating from a bar on the needle shroud 3 between the longitudinal main track 12.1 and the short longitudinal track 12.3 skews over the main track 12.1 at about the same angle as the bevel track 12.2 in a manner to guide the pin 10.2 into the bevel track 12.2 when moving from position C in the distal direction D. The resilient latch 3.1 is deflected aside by the pin 10.2 on translation from position PB into position PC but immediately returns to its initial position behind the pin 10.2 preventing it from returning to position PA or PB from position PC.

In the initial state the pin 10.2 is in position PA.

The needle shroud 3 is arranged to be translated in the housing 2 in the longitudinal direction. In the initial state the needle shroud 3 is in an initial position protruding from the proximal end P. The pin in position PA links the needle shroud 3 to the coupling carrier 10 in a manner to prevent further translation of the needle shroud 3 in the proximal direction P. The coupling carrier 10 is engaged to the plunger 11 by the resilient arms 10.1 caught behind the first plunger shoulder 11.2. The plunger 11 is engaged to the thrust collar 7 through the transversal arm 11.1 and the teeth 7.2. The thrust collar 7 is latched to the trigger button 8 through resilient first latches 8.1 on the trigger button 8 engaged in respective windows in the thrust collar 7. The first latches 8.1 are in a ramped engagement with the thrust collar 7 so as to deflect the first latches 8.1 outwards on axial load for disengaging them from the thrust collar 7. However, a second rib 2.2 in the housing 2 is in a ramped engagement with the first latches 8.1 preventing outward deflection of the first latches 8.1 in the initial state. Resilient second latches 8.2 on the trigger button 8 also abut proximally against the second rib 2.2 in the housing 2. The second latch 8.2 and the second rib 2.2 are in a ramped engagement trying to deflect the second latch 8.2 inwards on axial load. However, in the initial state, inward deflection is prevented by the needle shroud 3 inwardly supporting the second latches 8.2. Hence, the trigger button 8 cannot be depressed and translation of all internal components of the auto-injector 1 in the proximal direction P is prevented.

In order to prepare for an injection, a protective needle sheath 13 arranged for protecting a hollow injection needle 14 on the proximal end of the syringe 5 has to be removed. This may be achieved by means of a cap (not shown) which grips the needle shield 13, thereby removing the needle shield 13 when the cap is removed.

Figure 3B:
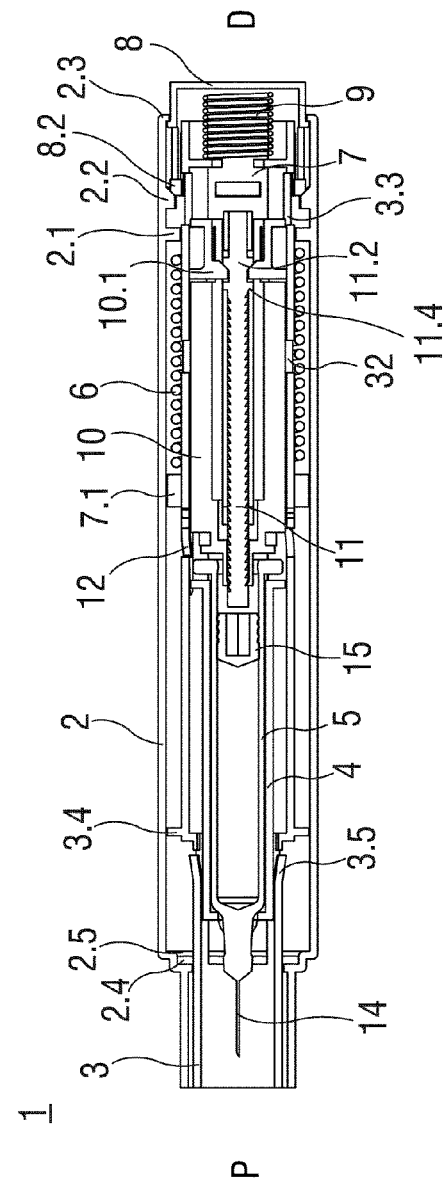

In order to start an injection cycle the proximal end P of the auto-injector 1 is pressed against an injection site, e.g. a patient's skin. Hence, the needle shroud 3 translates into the housing 2 into a depressed position (see FIG. 3a, 3b) further compressing the control spring 9. The needle shroud 3 is removed from behind the second latches 8.2 allowing them to be inwardly deflected into second apertures 3.3 in the needle shroud 3 near its distal end. As the needle shroud 3 is translated relative to the coupling carrier 10 the pin 10.2 is translated from position PA into position PB.

Figure 5:
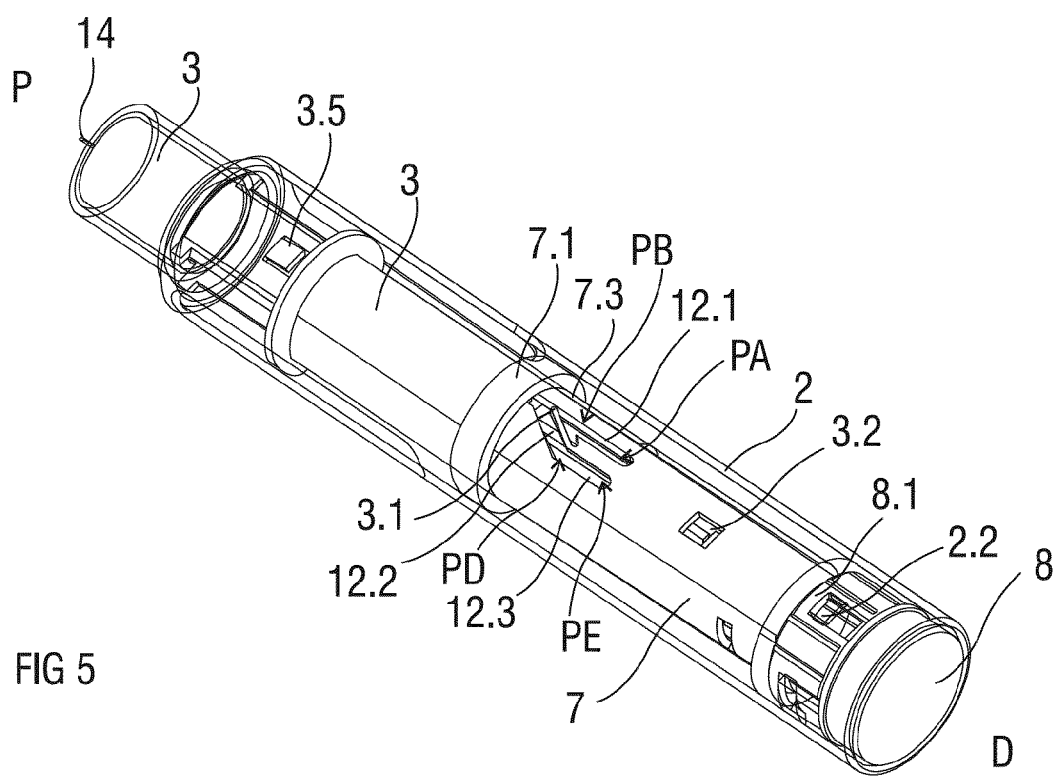
FIG. 5 is an isometric view of the auto-injector with a needle advanced for piercing a patient's skin.

The trigger button 8 may now be depressed resulting in inward deflection of the second latches 8.2 due to their ramped engagement to the second rib 2.2. As the trigger button 8 is still coupled to the thrust collar 7, plunger 11, coupling carrier 10, syringe carrier 4 and the syringe 5 this subassembly translates in the proximal direction P. The first latch 8.1 comprises a proximal ramped face engaged to the second rib 2.2 having a correspondent distal ramped face. The first latch 8.1 also has a distal ramped face engaged to a proximal ramped face on the aperture in the thrust collar 7. The ramped faces on the first latches 8.1, aperture in thrust collar 7 and second rib 2.2 will effectively wedge the first latches 8.1 in position and hold trigger button 8 in place, until such time as it is pushed in the proximal direction P. Then, the first latches 8.1 are forced past the ramped face on the second rib 2.2 and at that point the drive spring 6 will take over, pulling the trigger button 8 forward. This gives a 'fast trigger' feature to the auto-injector 1, preventing the user from hesitantly depressing the trigger button 8 halfway leaving the auto-injector 1 in an undefined state neither triggered nor safe. As the first latches 8.1 have passed behind the second rib 2.2 they are allowed to be outwardly deflected due to their ramped engagement in the windows of the trust collar 7 decoupling the trigger button 8 from the thrust collar 7. This releases the drive spring 6 which now translates the thrust collar 7, plunger 11, coupling collar 10, syringe collar 4 and syringe 5 in the proximal direction P for inserting the needle 14 beyond the proximal end P into an injection site, e.g. a patient's skin (see FIG. 5). Once the second latches 8.2 have passed the second rib 2.2 they are free to return to their original radial position, and in so doing latch in front of the proximal face of the second rib 2.2 thereby holding the trigger button 8 in the depressed position.

Due to this translation, the pin 10.2 moves from position PB to position PC deflecting the resilient latch 3.1 on its way, wherein the resilient latch 3.1 returns into its previous position behind the pin 10.2 preventing it from returning into position PA or PB.

An injection depth of the injection needle 14 is defined by a front stop 4.1 on the syringe carrier 4 hitting an inner proximal housing shoulder 2.4 in the housing 2. When the injection needle 14 has reached the injection depth the pin 10.2 has reached position PC in the longitudinal main track 12.1 staying just clear of the end of the longitudinal main track 12.1 to avoid damage.

Shortly before the needle 14 reaches the injection depth the resilient arms 10.1 arrive at the first aperture 3.2 in the needle shroud 3. With the syringe carrier 4 abutted against the housing 2 the syringe carrier 4 and the coupling carrier 10 cannot move further while axial load from the drive spring 6 on the plunger 11 is maintained. Consequently, the first plunger shoulder 11.2 deflects the resilient arms 10.1 outwards into the first aperture 3.2 decoupling the plunger 11 from the coupling carrier 10. The plunger 11 is translated further in the proximal direction P taking the stopper 15 with it thus injecting thus injecting the medicament through the injection needle 14 into the injection site. When the auto-injector 1 is removed from the injection site at the end of the injection or mid injection after partial delivery the needle shroud 3 translates in the proximal direction P under load of the control spring 9 into its initial position. As the coupling carrier 10 remains in position the pin 10.2 travels up the bevel track 12.2 into position PD thereby forcing the coupling carrier 10 to rotate relative to the needle shroud 3 which is splined to the housing 2. As the thrust collar 7 is keyed to the needle shroud 3 it stays in position while the plunger 11 is rotated with the coupling carrier 10. Thus the teethed transversal arm 11.1 rotates out of engagement with the teeth 7.2 on the thrust collar 7. The drive spring 6 still pushing on the thrust collar 7 is thus no longer coupled to the plunger 11. Thus, even if the auto-injector 1 is removed from the injection site mid injection the injection stops thus preventing medicament leaking out of the needle 14 post injection.

Figure 6:
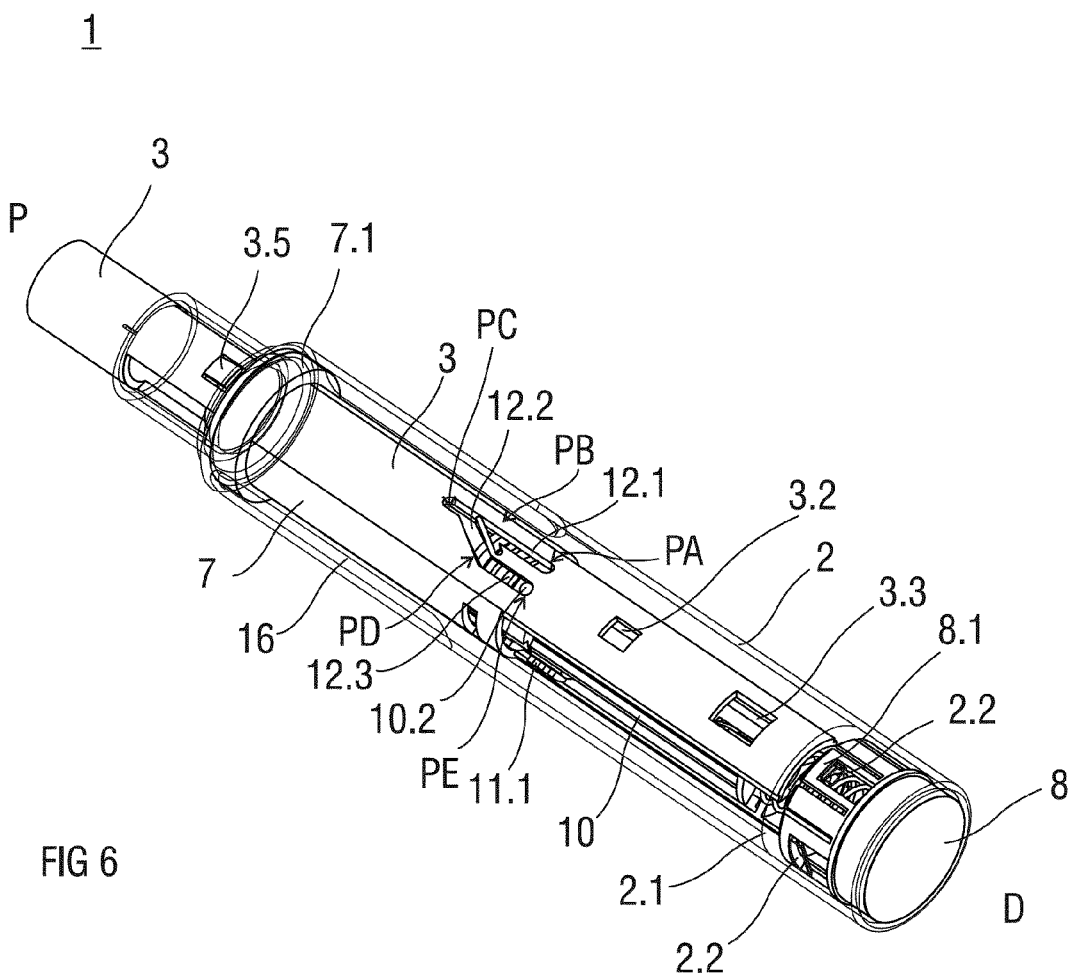
FIG. 6 is an isometric view of the auto-injector with the needle shroud advanced for covering the needle post injection.

Instead, the thrust collar 7 is translated in the proximal direction P taking the needle shroud 3 with it by hitting a shroud shoulder 3.4 on the needle shroud 3 until the shroud shoulder 3.4 abuts against an outer proximal housing shoulder 2.5 thus covering the needle 14. Due to that motion the pin moves to position PE. A pair of resilient clips 3.5 in the needle shroud 3 deflects outwards proximally behind the inner proximal housing shoulder 2.4 so as to prevent the needle shroud 3 from being depressed again so the needle 14 cannot be re-exposed (see FIG. 6).

The plunger 11 illustrated in the embodiment exhibits a rack feature 11.3 (cf. FIG. 4) which may be engaged by a corresponding feature in the coupling carrier 10 for providing an audible and/or tactile feedback that the injection is taking place thus. The end of the noise or vibration generated indicates to the user that the entire content of the syringe 5 has been delivered and the auto-injector 1 may be removed from the injection site.

A viewing window 16 is arranged in the housing 2 for inspecting the syringe contents prior to and during injection. After removal of the auto-injector 1 from the injection site the thrust collar 7 is visible through the viewing window 16 instead of the syringe 5 indicating that the auto-injector 1 has been used.

The auto-injector 1 may preferably be used for subcutaneous or intra-muscular injection, particularly for delivering one of an analgetic, an anticoagulant, insulin, an insulin derivate, heparin, Lovenox, a vaccine, a growth hormone, a peptide hormone, a protein, antibodies and complex carbohydrates.

The invention claimed is:

1. An Auto-injector for delivering a liquid medicament, comprising:
an elongate housing arranged to contain a syringe with a hollow injection needle and a stopper for sealing the syringe and displacing the medicament, the housing having a distal end and a proximal end with an orifice intended to be applied against an injection site, wherein the syringe is slidably arranged with respect to the housing;
a spring mechanism capable of, upon activation:
pushing the needle from a covered position inside the housing into an advanced position through the orifice and past the proximal end for insertion into the injection site,
operating the syringe to inject a dose of medicament, and
advancing a needle shroud in a proximal direction relative to the housing and over the needle for providing needle safety; and
an activating mechanism arranged to lock the spring mechanism in a pressurized state prior to manual operation and capable of, upon manual operation, releasing the spring mechanism,
wherein the spring mechanism is a single drive spring in the form of a compression spring directly engaged to the distal end of the housing and proximally bearing against a thrust collar arranged to transmit load from the spring mechanism via a plunger to the syringe and/or the stopper for needle insertion and injection, wherein the plunger is engageable to the thrust collar for joint axial translation, and wherein the plunger is disengageable from the thrust collar on relative rotation so as to allow the thrust collar to be advanced further by the drive spring in order to directly engage the needle shroud for advancing the needle shroud proximally over the needle.

2. The auto-injector according to claim 1, wherein the needle shroud is biased in a proximal direction so as to be in an initial position protruding from the proximal end in an initial state, wherein the activating mechanism comprises a trigger button interlocked to the needle shroud in such a manner that the needle shroud prevents manual operation of the trigger button when in the initial position, wherein the needle shroud is arranged to release the interlock on translation in a distal direction into a depressed position so as to allow manual operation of the trigger button.

3. The auto-injector according to claim 2, wherein the needle shroud is arranged to rotate the plunger on removal of the auto-injector from the injection site by translating from the depressed position into the initial position due to the bias, wherein the thrust collar is arranged to translate the needle shroud further into a needle safe position.

4. The auto-injector according to claim 3, wherein the plunger is slidably arranged within and keyed to a coupling carrier for joint rotation, wherein the coupling carrier is coupled to the syringe for joint translation, wherein the coupling carrier is connected to the needle shroud by a pin engaged in a shifting gate with a one-way feature in such manner that the pin is guided in a longitudinal main track of the shifting gate on translation of the needle shroud from the initial position into the depressed position and on translation of the syringe during needle insertion, wherein the one-way feature is arranged to be passed by the pin on needle insertion, wherein the one-way feature is arranged to guide the pin into a bevel track at a bifurcation of the shifting gate on translation of the needle shroud from the depressed position into the initial position thus rotating the coupling carrier and the plunger for disengaging it from the thrust collar.

5. The auto-injector Auto injector according to claim 4, wherein the plunger comprises a teethed transversal arm at the distal end engageable in corresponding teeth on an inner surface of the thrust collar, wherein the coupling carrier exhibits a longitudinal slot extending from its distal end almost to its proximal end, the slot having a width corresponding to a width of the transversal arm so as to key the plunger to the coupling carrier for joint rotation while allowing relative translation.

6. The auto-injector according to claim 4, wherein at least one resilient arm on the coupling carrier are arranged to engage a first plunger shoulder in the plunger in a manner to couple the plunger and the coupling carrier for joint axial translation, wherein the resilient arm and the first plunger shoulder are in a ramped engagement so as to deflect the resilient arm outwards on axial load for decoupling the plunger from the coupling carrier, wherein the needle shroud is arranged to outwardly support the resilient arm so as to prevent outward deflection and decoupling, wherein at least one first aperture is provided in the thrust collar for allowing outward deflection of the resilient arms when the needle has at least almost reached an injection depth.

7. The auto-injector according to claim 2, wherein the trigger button is arranged at the distal end in a manner to trigger an injection on depression into the housing in the proximal direction against the bias of a control spring arranged between the trigger button and the needle shroud for biasing the trigger button and the needle shroud against each other into their respective initial positions.

8. The auto-injector according to claim 7, wherein the thrust collar exhibits at least one window for engaging a respective resilient first latch on the trigger button, wherein the first latch is in a ramped engagement with the thrust collar so as to deflect it outwards on axial load for disengaging it from the thrust collar, wherein a second rib is arranged in the housing for preventing outward deflection of the first latch, wherein the first latch is arranged to be dislocated from the second rib on depression of the trigger button so as to allow outward deflection for releasing the drive spring.

9. The auto-injector according to claim 8, wherein at least one resilient second latch is arranged on the trigger button for proximally abutting against the second rib, wherein the second latch and the second rib are in a ramped engagement so as to deflect the second latch inwards on axial load, wherein the needle shroud is arranged to inwardly support the second latch in the initial position so as to prevent inward deflection, wherein the needle shroud exhibits at least one second aperture arranged to be moved inwardly behind the second latch for allowing inward deflection in the depressed position of the needle shroud.

10. The auto-injector according to claim 4, wherein the plunger comprises a rack feature for generating an audible and/or tactile feedback when translating relative to the coupling carrier having a corresponding feature for engaging the rack feature.

11. The auto-injector according to claim 4, wherein a syringe carrier is arranged to hold the syringe and support it at its proximal end, wherein the syringe carrier is translatable in a longitudinal direction within the housing, wherein the syringe carrier is coupled to the coupling carrier for joint axial translation in the longitudinal direction.

12. The auto-injector according to claim 1, wherein the needle shroud comprises at least one outwardly biased resilient clip arranged to engage to the housing in a needle safe position for preventing translation of the needle shroud in the distal direction.

13. The auto-injector according to claim 7, wherein the trigger button is arranged to be locked in the housing after having been depressed.

14. The auto-injector according to claim 8, wherein the first latch is in a ramped engagement with the thrust collar wedging the first latch in position between the second rib and the thrust collar, wherein the wedged engagement of the first latch between the second rib and the thrust collar is arranged to allow depression of the trigger button, wherein on at least partial depression of the trigger button the first latch is forced past the ramp on the second rib releasing the wedged engagement and allowing the drive spring to pull the trigger button fully into the depressed position.

\* \* \* \* \*